US008729056B2

(12) United States Patent
Ishizaka et al.

(10) Patent No.: US 8,729,056 B2
(45) Date of Patent: May 20, 2014

(54) PREVENTIVE AND/OR THERAPEUTIC AGENT OF HAND-FOOT SYNDROME

(75) Inventors: Kazuhiro Ishizaka, Tokyo (JP); Tadashi Nomizu, Koriyama (JP); Aya Kitao, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/637,760

(22) PCT Filed: Mar. 30, 2011

(86) PCT No.: PCT/JP2011/058071
§ 371 (c)(1),
(2), (4) Date: Sep. 27, 2012

(87) PCT Pub. No.: WO2011/125763
PCT Pub. Date: Oct. 13, 2011

(65) Prior Publication Data
US 2013/0045956 A1 Feb. 21, 2013

(30) Foreign Application Priority Data

Mar. 31, 2010 (JP) ................................ 2010-082379
Nov. 8, 2010 (JP) ................................ 2010-250168

(51) Int. Cl.
*A61K 31/44* (2006.01)
*A61K 31/47* (2006.01)
*A61K 31/415* (2006.01)
*A61K 31/135* (2006.01)

(52) U.S. Cl.
USPC ........... 514/171; 514/305; 514/307; 514/385; 514/396; 514/649

(58) Field of Classification Search
USPC .......................... 514/385, 396, 305, 307, 649
See application file for complete search history.

(56) References Cited

U.S. PATENT DOCUMENTS

| | | | |
|---|---|---|---|
| 6,060,083 A | 5/2000 | Dorr et al. | |
| 2008/0004247 A1 | 1/2008 | Lindmark et al. | |
| 2009/0062326 A1* | 3/2009 | Spindel et al. | ................ 514/291 |
| 2009/0306097 A1 | 12/2009 | Rodemer | |

FOREIGN PATENT DOCUMENTS

| | | |
|---|---|---|
| EP | 2 368 549 | 9/2011 |
| JP | 2008-506674 | 3/2008 |
| JP | 2009-542581 | 12/2009 |
| JP | 2010-018564 | 1/2010 |
| WO | 00/52013 | 9/2000 |
| WO | 2007/046102 | 4/2007 |
| WO | 2009/100367 | 8/2009 |
| WO | 2009/150408 | 12/2009 |

OTHER PUBLICATIONS

Pahl, A., et al. Biochemical Pharmacology vol. 72 pp. 1690-1696. Published 2006.*
Homma, Y. et al., International Journal of Urology vol. 15, pp. 809-815. Published 2008.*
Nagore, E., et al. Am. J. Clin. Dermatol. vol. 1 pp. 225-233, published 2000.*
International Search Report issued May 10, 2011 in International (PCT) Application No. PCT/JP2011/058071, of which the present application is the national stage.
R. Heald, "Anticholinergic drugs as antiperspirants", American Perfumer and Cosmetics, vol. 81, Oct. 1996, pp. 95-98.
M. Hensley et al., "Sunitinib malate in the treatment of recurrent or persistent uterine leiomyosarcoma: A Gynecologic Oncology Group phase II study", Gynecologic Oncology, vol. 115, 2009, pp. 460-465.
T. Ahmad et al., "Kinase Inhibition with BAY 43-9006 in Renal Cell Carcinoma", Clinical Cancer Research, vol. 10, Sep. 15, 2004, pp. 6388s-6392s.
Written Opinion of the International Searching Authority issued May 10, 2011 in International (PCT) Application No. PCT/JP2011/058071.
U. Jacobi et al., "Release of doxorubicin in sweat: first step to induce the palmar-planter erythrodysesthesia syndrome?", Annals of Oncology, vol. 16, pp. 1210-1211, 2005.
C. Fabian et al., "Pyridoxine therapy for palmer-plantar erythrodysesthesia associated with continuous 5-fluorouracil infusion", Investigational New Drugs, vol. 8, pp. 57-63, 1990.
Hand-foot Syndrome Atlas, edited by Tetsuya Taguchi, Chugai Pharmaceutical Col, Ltd., 2007, with partial translation.
L. Jain et al., "Lack of Association Between Excretion of Sorafenib in Sweat and Hand-Foot Skin Reaction", Pharmacotherapy, vol. 30, pp. 52-56, 2010.
Extended European Search Report issued Jul. 23, 2013 in corresponding European patent application No. 11 76 5663.
Joan D. Webster-Gandy et al., "Palmar-plantar erythrodysesthesia (PPE): A literature review with commentary on experience in a cancer centre", European Journal of Oncology Nursing, vol. 11, No. 3, Jul. 1, 2007, pp. 238-246.

\* cited by examiner

*Primary Examiner* — Paul Zarek
*Assistant Examiner* — George W Kosturko
(74) *Attorney, Agent, or Firm* — Wenderoth, Lind & Ponack, L.L.P.

(57) ABSTRACT

The agent for the prevention and/or treatment of Hand-Foot Syndrome comprising a compound with anticholinergic activity can be provided. The agent for the prevention and/or treatment of Hand-Foot Syndrome comprising a compound with anticholinergic activity can be safely administered to the patients with Hand-Foot Syndrome, and has shown the superior preventive and/or treatment effect against Hand-Foot Syndrome.

10 Claims, 6 Drawing Sheets

PREVENTIVE AND/OR THERAPEUTIC AGENT OF HAND-FOOT SYNDROME

TECHNICAL FIELD

The present invention relates to an agent for the prevention and/or treatment of Hand-Foot Syndrome comprising a compound with anticholinergic activity.

BACKGROUND ART

Hand-Foot Syndrome is a skin disease developed as a side effect of anti-cancer drug treatment and therefore is an indicator of the dose limiting factor of an anti-cancer drug. Favorite sites of Hand-Foot Syndrome are distal portions of the extremities, especially, the palms, soles, and nails and it often appears at these sites with erythema or pigmentation. Patients with mild symptoms (grade 1 of Hand-Foot Syndrome judging criteria) are not limited in the activities of daily living. However, in severe cases, patients develop swelling or redness with pain (grade 2 of said criteria). In addition, cornification or desquamation of the palms and soles become prominent, and sometimes a skin fissure develops, which is accompanied by hyperesthesia. Patients with such conditions might experience difficulty in holding things or in ambulation because of the pain (grade 3 of said criteria).

The pathogenic mechanism of Hand-Foot Syndrome is currently unexplained. For example, there are some factors, such as the inhibition of proliferating ability of cutaneous basal cell, the leakage of an anti-cancer drug from blood vessels (e.g., see Patent Document 1), or the secretion of an anti-cancer drug from the eccrine gland (e.g., see Nonpatent Document 1), which are suggested as one of the possible causes of Hand-Foot Syndrome. However, the causal connection between the pathogenesis of the same and an anti-cancer drug is yet unknown.

As mentioned above, the pathogenic mechanism of Hand-Foot Syndrome is unknown and therefore no prevention method or treatment method is established. the current treatment method of Hand-Foot Syndrome is mainly symptomatic treatment relying on empirical treatment such as: resting the limbs, or in the situation of severe swelling, cooling the limbs or elevating the limbs; a local treatment using an external formulation such as urea ointment, a heparinoid preparation or vitamin ointments for moisturizing purposes; a local treatment using a topical steroid with an anti-inflammatory effect; a systemic treatment using an internal remedy such as prednisolone, dexamethasone, or pyridoxine hydrochloride (Vitamin B6) (e.g., see Nonpatent Document 2); and for treatments of symptoms on the nail, washing, protecting with gauze, taping, onychoplasty, an artificial nail, cryosurgery, and so on.

In addition to the above, for example, the following treatments are also suggested: usage of local DMSO for the treatment of Hand-Foot Syndrome caused by liposomal doxorubicin (e.g., see Patent Document 1), usage of dihydropyrimidine dehydrogenase, thymidine phosphorylase, and/or an uridine phosphorylase enzyme inhibitor for the treatment of Hand-Foot Syndrome caused by fluorouracil or its precursor (e.g., see Patent Document 2), and usage of a cyclin-dependent kinase II inhibitor for prevention and/or reduction of severity of epithelial cytotoxicity side effects including Hand-Foot Syndrome caused by chemotherapy and/or radiation therapy (e.g., see Patent Document 3).

However, the effects of the aforementioned treatments are not satisfactory.

In addition, there are cases where the administration of responsible agents might have to be interrupted as there is no means to treat such symptoms. Nevertheless, for example, in a Phase 2 clinical study of capecitabine in Japan, it was reported that the period for recovery of Hand-Foot Syndrome for patients with the highest Hand-Foot Syndrome judging criteria grade of 3 after interruption is about two to three months on average (e.g., see Nonpatent Document 3), which shows the fact that it takes a long time for its recovery even with interruption.

Thus, a more effective drug product with instant results is demanded.

On the other hand, as for Hand-Foot Syndrome, there are some reports indicating the connectivity of its pathogenesis with sweat. For example, Patent Document 4 discloses an adhesive skin patch for patients under anti-cancer drug treatment, which contains an adhesive base, and at least one compound selected from the group consisting of oil, a polyhydric alcohol, and a hydrophilic high-molecular compound. It is described that the aforementioned skin adhesive patch is effective against Hand-Foot Syndrome by preventing sweat or sebum which contains such an anti-cancer drug to be stored in the skin and by absorbing sweat or sebum which contains the anti-cancer drug. However, this document focused on the fact that use of certain skin adhesive patches to remove the anti-cancer drug contained in the sweat or sebum is effective for Hand-Foot Syndrome. Furthermore, in this document, the anti-cancer drug that caused the pathogenesis of Hand-Foot Syndrome is not specified and this document does not describe which route of blood vessels and eccrine glands is important as a secretion pathway of the anti-cancer drug to the sweat or sebum.

On the other hand, it is described in Nonpatent Document 1 that the anti-cancer drug doxorubicin was detected in sweat from patients with Hand-Foot Syndrome who were administered with such a drug and that they were associated with hyperhidrosis, which implies the connectivity of Hand-Foot Syndrome with hyperhidrosis. However, it is not validated in this document the connectivity of the pathogenesis of Hand-Foot Syndrome with the drug substance in the sweat. This document suggests usage of an antiperspirant such as iontophoresis or aluminum chloride to suppress the pathogenesis of Hand-Foot Syndrome as the nature of this document is to associate Hand-Foot Syndrome with sweat. Although it has been five years since this document was published, it shows no successful experience of suppressing pathogenesis of Hand-Foot Syndrome using such antiperspirant.

Currently, the causal association between Hand-Foot Syndrome and the secretion of a drug substance into sweat is being questioned (e.g., see Nonpatent Document 4). It was described in this document that a drug substance was not detected in sweat from patients with Hand-Foot Syndrome caused by the anti-cancer drug sorafenib administration, and therefore there is no relationship between Hand-Foot Syndrome caused by sorafenib and the secretion of a drug substance in sweat. Finally, it concluded that further studies are needed to understand the mechanism of Hand-Foot Syndrome.

As mentioned above, the development of prevention and/or treatment methods of Hand-Foot Syndrome is essential and indispensable in order to continue anti-cancer therapy. However, no effective method has been established.

PRIOR ART DOCUMENTS

Patent Document

[Patent Document 1] U.S. Pat. No. 6,060,083
[Patent Document 2] WO2009/100367
[Patent Document 3] WO2000/052013
[Patent Document 4] JP-A No. 2010-18564 gazette Nonpatent Document

[Nonpatent Document 1] Annals of Oncology, vol. 16, p. 1210-1211, 2005
[Nonpatent Document 2] Investigational New Drugs, vol. 8, p. 57-63, 1990
[Nonpatent Document 3] Hand-foot Syndrome Atlas, edited by Tetsuya Taguchi (2007) Chugai Pharmaceutical Col, Ltd.
[Nonpatent Document 4] Pharmacotherapy, vol. 30, p. 52-56, 2010

SUMMARY OF THE INVENTION

Problems to be Solved by the Invention

Hand-Foot Syndrome is a severe side effect induced by the administration of an anti-cancer drug, and dose reduction, interruption or discontinuation of the anti-cancer drug is one of the effective methods to ease and relieve its symptoms. However, this reduces the effectiveness of the cancer treatment which is the original aim, and it means that there is a cessation/discontinuation of the cancer treatment. Thus it cannot be said that it is an appropriate countermeasure against the side effect induced by the cancer treatment. There is no known pharmacological agent which has a satisfactory effect against Hand-Foot Syndrome, and current treatment methods are relying on dose reduction, interruption, or discontinuation of the anti-cancer drug. Therefore, it is essential to establish a new effective prevention and/or treatment method of Hand-Foot Syndrome to continue proper cancer treatment.

Accordingly, the purpose of the present invention is to provide a safe pharmacological agent which possesses a superior prevention and/or treatment effect against Hand-Foot Syndrome.

Means for Solving the Problems

The present inventors have conducted intensive studies in an attempt to solve the above-mentioned problems and found that a compound with anticholinergic activity (an anticholinergic drug) surprisingly possesses a superior prevention and/or treatment effect against Hand-Foot Syndrome, and completed the present invention. The effect is remarkable and it was completely unpredictable to those in the art. As it is shown concretely in the examples of this application, when an anticholinergic drug is administered to patients with severe Hand-Foot Syndrome caused by anti-cancer drug treatment, the result is, amazingly, that the remarkable relief of symptoms was recognized in only several days to several weeks after the commencement of its administration.

An anticholinergic drug is a general term for drugs that are effective to inhibit the mechanism of acetylcholine which deliver the stimulus from parasympathetic nervous, and it is used for the following purposes: a treatment for gastritis or a gastric ulcer by mainly inhibiting the secretion of gastric acid; a treatment for bronchial asthma, chronic bronchitis, or pneumonectasia by inhibiting the contraction of bronchi; a treatment for urinary urgency, frequent urination, or urge incontinence arising from an overactive bladder; and so on. Also, an anticholinergic drug is known to have antiperspirant action. Secretion of sweat is caused by the release of acetylcholine to sweat glands from a sympathetic nerve, and therefore it is supposed that an anticholinergic drug is effective to inhibit diaphoresis.

On the other hand, according to Genpatsusei Kyokusho Takansho Shinryo Gaidorain (Guideline for the treatment of primary local hyperhidrosis) (Japanese Journal of Dermatology, 120(8), 1607-1625, 2010) published by Japanese Dermatological Association, the grade of recommendation of an anticholinergic drug as an antiperspirant is "C1", a grade which is deemed to lack sufficient evidence to be effective as antiperspirant.

As mentioned in the Technical Field of this specification, it is described in Nonpatent document 1 that use of an antiperspirant, such as iontophoresis or aluminum chloride, which is effective for hyperhidrosis treatment, is suggested to suppress the pathogenesis of Hand-Foot Syndrome. However, considering the severity of the clinical condition of Hand-Foot Syndrome (especially grade 3 of Hand-Foot Syndrome judging criteria), it was considered unlikely that the use of an antiperspirant can ease such severe symptoms. Furthermore, according to Genpatsusei Kyokusho Takansho Shinryo Gaidorain (Guideline for the treatment of primary local hyperhidrosis), there is a risk of worsening skin problems if aluminum chloride is used for patients with Hand-Foot Syndrome with skin problems as one of its side effects is irritant dermatitis. Also, iontophoresis takes time to show its efficacy, and therefore an immediate result cannot be expected. Thus the efficacy has been questioned even though use of an antiperspirant was suggested to suppress the pathogenesis of Hand-Foot Syndrome in Nonpatent Document 1, and therefore it has been ignored and, as mentioned at the beginning, the current available treatments for Hand-Foot Syndrome are limited to symptomatic treatment.

On the other hand, there is no suggestion of using an anticholinergic drug as an antiperspirant in Nonpatent Document 1, and the effect of an anticholinergic drug as an antiperspirant for hyperhidrosis treatment was not established as much as iontophoresis or aluminum chloride. Thus, there is no evidence to actively support the use of an anticholinergic drug because there is no sufficient evidence relating to its effect as an antiperspirant.

In addition, it is not possible for those in the art to predict the remarkable palliative effect of an anticholinergic drug observed on the patients with severe Hand-Foot Syndrome only after several days to several weeks of its administration.

By using an anticholinergic drug for the treatment of Hand-Foot Syndrome caused by an anti-cancer drug, there would be no cause of dose reduction, interruption or discontinuation of the anti-cancer drug. Therefore, it is a breakthrough countermeasure at the point which can treat the side effects of the cancer treatment, without weakening the effect of the cancer treatment, which is the original aim, or ceasing/discontinuing the cancer treatment.

That is, the present invention relates to:
[1] an agent for the prevention and/or treatment of Hand-Foot Syndrome comprising a compound with anticholinergic activity;
[2] the agent according to above [1], wherein the compound with anticholinergic activity is a muscarinic receptor antagonist;
[3] the agent according to above [2], wherein the muscarinic receptor antagonist is a M3 muscarinic receptor antagonist;
[4] the agent according to above [3], wherein the M3 muscarinic receptor antagonist is one or more compounds selected from the group consisting of a M3 selective muscarinic receptor antagonist, an antagonist selective for M1 and M3 muscarinic receptor and a subtype nonselective muscarinic receptor antagonist;
[5] the agent according to above [4], wherein the compound is a compound selected from the group consisting of imidafenacin, solifenacin, tolterodine and fesoterodine, and a pharmaceutically acceptable salt, solvate and prodrug thereof;

[6] the agent according to above [4], wherein the compound is a compound selected from the group consisting of imidafenacin, solifenacin and tolterodine, and a pharmaceutically acceptable salt, solvate and prodrug thereof;

[7] the agent according to above [5], wherein the compound is a compound selected from the group consisting of imidafenacin, solifenacin succinate, tolterodine tartrate and fesoterodine fumarate;

[8] the agent according to above [6], wherein the compound is a compound selected from the group consisting of imidafenacin, solifenacin succinate and tolterodine tartrate;

[9] the agent according to above [1], wherein the Hand-Foot Syndrome is Hand-Foot Syndrome caused by administration of an anti-cancer drug;

[10] the agent according to above [9], wherein the anti-cancer drug is an antimetabolite or a molecularly-targeted drug;

[11] the agent according to above [10], wherein the antimetabolite is capecitabine and the molecularly-targeted drug is sunitinib malate or sorafenib tosilate;

[12] the agent according to above [1], wherein the prevention is recurrence prevention;

[13] the agent according to above [1], wherein the compound with anticholinergic activity is imidafenacin, a pharmaceutically acceptable salt, solvate or prodrug thereof;

[14] the agent according to above [1], wherein the compound with anticholinergic activity is solifenacin, a pharmaceutically acceptable salt, solvate or prodrug thereof;

[15] the agent according to above [1], wherein the compound with anticholinergic activity is tolterodine or fesoterodine, or a pharmaceutically acceptable salt, solvate or prodrug thereof;

[16] the agent according to above [1], wherein the compound with anticholinergic activity is tolterodine, a pharmaceutically acceptable salt, solvate or prodrug thereof;

[17] the agent according to above [1], wherein the compound with anticholinergic activity is imidafenacin;

[18] the agent according to above [1], wherein the compound with anticholinergic activity is solifenacin succinate;

[19] the agent according to above [1], wherein the compound with anticholinergic activity is tolterodine tartrate or fesoterodine fumarate;

[20] the agent according to above [1], wherein the compound with anticholinergic activity is tolterodine tartrate;

[21] the agent according to above [17], wherein the daily dose of imidafenacin is from 0.1 mg to 0.4 mg;

[22] the agent according to above [21], wherein the imidafenacin is orally administered twice a day in an amount per dose of 0.1 mg;

[23] the agent according to above [9], wherein the anti-cancer drug is an antimetabolite;

[24] the agent according to above [9], wherein the anti-cancer drug is a molecularly-targeted drug;

[25] the agent according to above [23], wherein the antimetabolite is capecitabine;

[26] the agent according to above [24], wherein the molecularly-targeted drug is sunitinib malate or sorafenib tosilate;

[27] a medicament comprising a combination of an agent for the prevention and/or treatment of Hand-Foot Syndrome comprising a compound with anticholinergic activity and one or more members selected from the group consisting of moisturizing agent, antibiotic, topical steroid, steroid for internal use, nonsteroidal anti-inflammatory drug and vitamin $B_6$ preparation;

[28] a medicament comprising a combination of an agent for the prevention and/or treatment of Hand-Foot Syndrome comprising a compound with anticholinergic activity and an anti-cancer drug;

[29] an agent for the prevention and/or treatment of Hand-Foot Syndrome comprising a combination of a compound with anticholinergic activity and one or more members selected from the group consisting of moisturizing agent, antibiotic, topical steroid, steroid for internal use, nonsteroidal anti-inflammatory drug and vitamin $B_6$ preparation;

[30] an agent for the prevention and/or treatment of Hand-Foot Syndrome comprising a combination of a compound with anticholinergic activity and an anti-cancer drug;

[31] a medicament comprising a combination of the agent described in above [1] and one or more members selected from the group consisting of moisturizing agent, antibiotic, topical steroid, steroid for internal use, nonsteroidal anti-inflammatory drug and vitamin $B_6$ preparation;

[32] a medicament comprising a combination of the agent described in above [1] and an anti-cancer drug;

[33] the agent according to above [1], used in combination with one or more members selected from moisturizing agent, antibiotic, topical steroid, steroid for internal use, nonsteroidal anti-inflammatory drug or vitamin $B_6$ preparation;

[34] the agent according to above [1], used in combination with an anti-cancer drug;

[35] an agent for the prevention and/or treatment of Hand-Foot Syndrome comprising imidafenacin, a pharmaceutically acceptable salt, solvate or prodrug thereof;

[36] an agent for the prevention and/or treatment of Hand-Foot Syndrome comprising solifenacin, a pharmaceutically acceptable salt, solvate or prodrug thereof;

[37] an agent for the prevention and/or treatment of Hand-Foot Syndrome comprising tolterodine or fesoterodine, or a pharmaceutically acceptable salt, solvate or prodrug thereof;

[38] an agent for the prevention and/or treatment of Hand-Foot Syndrome comprising tolterodine, a pharmaceutically acceptable salt, solvate or prodrug thereof;

[39] a method for the prevention and/or treatment of Hand-Foot Syndrome, which comprises administering an effective amount of a compound with anticholinergic activity to a mammal;

[40] a compound with anticholinergic activity for use in the prevention and/or treatment of Hand-Foot Syndrome;

[41] Use of a compound with anticholinergic activity for the manufacture of an agent for the prevention and/or treatment of Hand-Foot Syndrome;

[42] a method for the prevention and/or treatment of Hand-Foot Syndrome, which comprises administering an effective amount of a compound with anticholinergic activity to a patient in need of the prevention and/or treatment thereof;

[43] a method for the treatment of Hand-Foot Syndrome, which comprises administering an effective amount of a compound with anticholinergic activity to a patient who developed Hand-Foot Syndrome;

[44] a method for the prevention of Hand-Foot Syndrome, which comprises administering an effective amount of a compound with anticholinergic activity to a subject having the potential to develop Hand-Foot Syndrome before onset of Hand-Foot Syndrome;

[45] use of a compound with anticholinergic activity for the prevention and/or treatment of Hand-Foot Syndrome;

[46] a method for the treatment of Hand-Foot Syndrome, which comprises administering an effective amount of a compound with anticholinergic activity to a patient in need of the treatment thereof;

[47] a method for the prevention of Hand-Foot Syndrome, which comprises administering an effective amount of a compound with anticholinergic activity to a subject in need of the prevention thereof before onset of Hand-Foot Syndrome.

Effect of the Invention

According to the present invention, an agent for the prevention and/or treatment of Hand-Foot Syndrome can be provided. Until now, dose reduction, interruption or discontinuation of the anti-cancer drug was inevitable to treat Hand-Foot Syndrome. However, the agent of this invention makes it possible to continue the cancer treatment, and then lead to an early recovery from the cancer. Furthermore, the quality of life (QOL) of patients improves together with the improvement of the Hand-Foot Syndrome.

MODE FOR CARRYING OUT THE INVENTION

Figure 1:
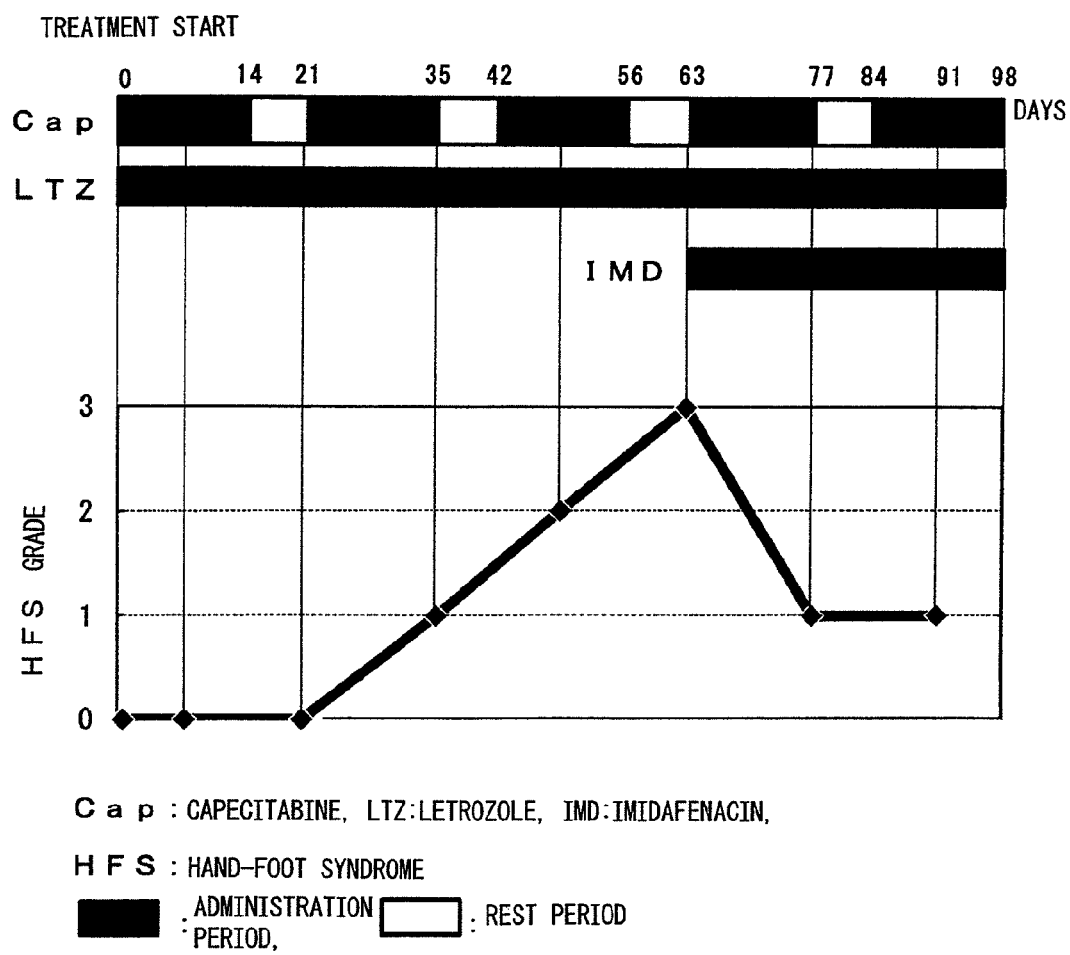
FIG. 1 It shows the effect of imidafenacin on Hand-Foot Syndrome caused by capecitabine administration. In the figure, Cap, LTZ, IMD, and HFS represent capecitabine, letrozole, imidafenacin, and Hand-Foot Syndrome, respectively.

In the present invention, the anticholinergic drug is also known as a parasympatholytic agent, and is not particularly limited so long as it functions as an acetylcholine receptor antagonist. An anticholinergic drug, for example, is a compound with antagonistic activity against the muscarinic receptor (muscarinic receptor antagonist), and preferably a compound with antagonistic activity against the M3 muscarinic receptor (M3 muscarinic receptor antagonist). An M3 muscarinic receptor antagonist includes, for example, an M3 selective muscarinic receptor antagonist, an antagonist selective for the M1 and M3 muscarinic receptor, a subtype non-selective muscarinic receptor antagonist, etc.

Also, in the present invention, the anticholinergic drug can be any combination of more than two different compounds. Specifically, for example, it can be a combination of an M1 selective muscarinic receptor antagonist and an M3 selective muscarinic receptor antagonist, etc.

The muscarinic receptor antagonist includes, for example, pirenzepine (CAS No. 28797-61-7), solifenacin (CAS No. 242478-37-1), darifenacin (CAS No. 133099-04-4), oxitropium (CAS No. 99571-64-9), tiotropium (CAS No. 186691-13-4), darotropium (CAS No. 850689-51-9), tarafenacin (CAS No. 385367-47-5), acridinium (CAS No. 727649-81-2), glycopyrronium (CAS No. 13283-82-4), imidafenacin (CAS No. 170105-16-5), revatropate (CAS No. 149926-91-0), tolterodine (CAS No. 124937-51-5), fesoterodine (CAS No. 286930-02-7), propiverine (CAS No. 60569-19-9), cimetropium (CAS No. 150521-16-7), isopropamide (CAS No. 7492-32-2), orphenadrine (CAS No. 83-98-7), oxybutynin (CAS No. 5633-20-5), tridihexethyl (CAS No. 60-49-1), trospium (CAS No. 47608-32-2), atropine (CAS No. 51-55-8), scopolamine (CAS No. 51-34-3), butylscopolamine (CAS No. 7182-53-8), N-methylscopolamine (CAS No. 13265-10-6), clidinium (CAS No. 7020-55-5), cyclopentolate (CAS No. 512-15-2), emepronium (CAS No. 27892-33-7), flavoxate (CAS No. 15301-69-6), tropicamide (CAS No. 1508-75-4), hyoscyamine (CAS No. 101-31-5), methantheline (CAS No. 5818-17-7), oxyphencyclimine (CAS No. 125-53-1), prifinium (CAS No. 10236-81-4), procyclidine (CAS No. 77-37-2), propantheline (CAS No. 298-50-0), trihexyphenidyl (CAS No. 114-11-6), ipratropium (CAS No. 60205-81-4), homatropine (CAS No. 87-00-3), otilonium (CAS No. 105360-89-2), tiquizium (CAS No. 149755-23-7), butropium (CAS No. 107080-63-7), timepidium (CAS No. 97094-64-9), tiemonium (CAS No. 6252-92-2), oxapium (CAS No. 17834-29-6), piperidolate (CAS No. 82-98-4) or a pharmaceutically acceptable salt, solvate or prodrug thereof, or belladonna or botulinum toxin A, etc.

The M3 muscarinic receptor antagonist includes, for example, solifenacin, darifenacin, oxitropium, tiotropium, darotropium, tarafenacin, acridinium, glycopyrronium, imidafenacin, revatropate, tolterodine, fesoterodine, propiverine, cimetropium, isopropamide, orphenadrine, oxybutynin, tridihexethyl, trospium, atropine, scopolamine, butylscopolamine, N-methylscopolamine, clidinium, cyclopentolate, emepronium, flavoxate, tropicamide, hyoscyamine, methantheline, oxyphencyclimine, prifinium, procyclidine, propantheline, trihexyphenidyl, ipratropium, homatropine, otilonium, tiquizium, butropium, timepidium, tiemonium, oxapium, piperidolate, or a pharmaceutically acceptable salt, solvate or prodrug thereof, or belladonna or botulinum toxin A, etc.

The M1 selective muscarinic receptor antagonist includes, for example, pirenzepine hydrochloride (CAS No. 29868-97-1), pirenzepine hydrochloride hydrate, etc.

The M3 selective muscarinic receptor antagonist includes, for example, solifenacin (CAS No. 242478-37-1), solifenacin succinate (CAS No. 242478-38-2, Vesicare (registered trademark)), darifenacin hydrobromide (CAS No. 133099-07-7, Enablex (registered trademark)), oxitropium bromide (CAS No. 30286-75-0), tiotropium bromide (CAS No. 136310-93-5), tiotropium bromide hydrate (CAS No. 139404-48-1), darotropium bromide (CAS No. 850607-58-8), tarafenacin (CAS No. 385367-47-5), aclidinium bromide (CAS No. 320345-99-1), glycopyrronium bromide (CAS No. 475468-09-8), etc.

The antagonist selective for the M1 and M3 muscarinic receptor includes, for example, imidafenacin (CAS No. 170105-16-5, Staybla (registered trademark)/Uritos (registered trademark)), revatropate hydrobromide (CAS No. 262586-79-8), etc.

The subtype non-selective muscarinic receptor antagonist includes, for example, tolterodine (CAS No. 124937-51-5), tolterodine tartrate (CAS No. 124937-52-6, Detrusitol (registered trademark)), fesoterodine (CAS No. 286930-02-7), fesoterodine fumarate (CAS No. 286930-03-8, Toviaz (registered trademark)), propiverine (CAS No. 60569-19-9), propiverine hydrochloride (CAS No. 54556-98-8, Bup-4 (registered trademark)), cimetropium bromide (CAS No. 51598-60-8), isopropamide iodide (CAS No. 71-81-8), orphenadrine hydrochloride (CAS No. 341-69-5), oxybutynin (CAS No. 5633-20-5), oxybutynin hydrochloride (CAS No. 1508-65-2), tridihexethyl chloride (CAS No. 4310-35-4), trospium chloride (CAS No. 10405-02-4), atropine (CAS No. 51-55-8), atropine sulfate hydrate (CAS No. 5908-99-6), belladonna, botulinum toxin A, butylscopolamine bromide (CAS No. 149-64-4), clidinium bromide (CAS No. 3485-62-9), cyclopentolate hydrochloride (CAS No. 5870-29-1), emepronium bromide (CAS No. 3614-30-0), flavoxate hydrochloride (CAS No. 3717-88-2), glycopyrrolate (CAS No. 596-51-0), tropicamide (CAS No. 1508-75-4), hyoscyamine (CAS No. 101-31-5), methantheline bromide (CAS No. 53-46-3), methscopolamin bromide (CAS No. 155-41-9), oxyphencyclimine hydrochloride (CAS No. 125-52-0), prifinium bromide (CAS No. 4630-95-9), procyclidine (CAS No. 77-37-2), propantheline bromide (CAS No. 50-34-0), trihexyphenidyl hydrochloride (CAS No. 52-49-3), ipratropium bromide, ipratropium bromide hydrate (CAS No. 22254-24-6), homatropine hydrobromide (CAS No. 51-56-9), otilonium bromide (CAS No. 26095-59-0), tiquizium bromide (CAS No. 71731-58-3), butropium bromide (CAS No. 29025-14-7), timepidium bromide (CAS No. 35035-05-3), timepidium bromide hydrate, N-methylhyoscine methyl sulfate (CAS No. 18067-13-5), tiemonium iodide (CAS No. 144-12-7), oxapium iodide (CAS No. 6577-41-9), piperidolate hydrochloride (CAS No. 129-77-1), etc. Also, the anticholinergic drugs in the present invention do not only include ones which have been found out so far in the past but also those which will be discovered from now onward in the future. Furthermore, the anticholiergic drug in the present invention includes a free form, a pharmaceutically acceptable salt, a solvate, and a prodrug thereof, etc. In addition, the anticholinergic drug in the present invention includes all isomers unless otherwise specifically mentioned. For example, stereoisomers generated from asymmetric carbon atom(s) (R-, S-isomer, α-, β-configuration, enantiomer, diastereomer), mixtures thereof at voluntary ratios and racemic mixtures are all included in the anticholiergic drug in the present invention.

In the present invention, the anticholiergic drug is preferably imidafenacin, solifenacin, tolterodine or fesoterodine, or a pharmaceutically acceptable salt, solvate, or prodrug thereof. More preferably, it is imidafenacin, solifenacin succinate, tolterodine tartrate, or fesoterodine fumarate. Imidafenacin, a pharmaceutically acceptable salt, solvate, or prodrug thereof is even more preferred, and imidafenacin is especially preferred.

It is preferable that the aforementioned "pharmaceutically acceptable salt" in the present invention is nontoxic and water-soluble. Examples of a suitable salt include a salt of an alkali metal (e.g., potassium, sodium, lithium), a salt of an alkaline earth metal (e.g., calcium, magnesium), a ammonium salt (e.g., tetramethylammonium salt, tetrabutylammonium salt), a salt of an organic amine (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine), etc. Examples of a suitable acid addition salt include an inorganic acid salt such as hydrochloride, hydrobromide, hydroiodide, sulfate, phosphate, nitrate and so forth or an organic acid salt such as formate, propionate, malonate, succinate, maleate, fumarate, oxalate, acetate, lactate, malate, tartrate, benzoate, citrate, methanesulfonate, ethanesulfonate, benzene sulfonate, aspartate, glutamate, toluene sulfonate, isethionate, glucuronate, gluconate and so forth. The preferred salt in the present invention is an acid addition salt.

It is preferable that the aforementioned "solvate" in the present invention has low toxicity and is water-soluble. Examples of a suitable solvate include a solvate of water or an alcohol solvent (e.g., ethanol and so forth).

The anticholinergic drug can be converted into the aforementioned salt or solvate by methods known per se.

The aforementioned "prodrug" in the present invention refers to a compound which is converted into the aforementioned anticholinergic drug by reactions with enzymes, gastric acid and so on in vivo. The prodrug may be either a hydrate or a non-hydrate. Also, the prodrug may be converted into the anticholinergic drug under physiological conditions as described in "Iyakuhin No Kaihatsu" (Development of Pharmaceutical), Vol. 7, "Bunshi Sekkei" (Molecular Modelig), pp. 163-198 (Hirokawa Shoten, 1990). Furthermore, the anticholinergic drug may be labeled with a radioactive isotope (e.g., $^3H$, $^{14}C$, $^{35}S$, $^{125}I$), etc., and any atoms contained in the anticholinergic drug can be replaced with the corresponding stable isotope (e.g., deuterium $^2H$, bicarbonate $^{13}C$, heavy nitrogen $^{15}N$, heavy oxygen $^{17}O$ or $^{18}O$), etc.

Imidafenacin is 4-(2-Methyl-1H-imidazole-1-yl)-2,2-diphenylbutanamide.

Imidafenacin can be prepared by methods known per se, for example, the method described in JP-A No. 7-215943. Also, commercially available products (Staybla (registered trademark)/Uritos (registered trademark)), can be used as imidafenacin.

Solifenacin is (3R)-1-Azabicyclo[2.2.2]oct-3-yl(1S)-1-phenyl-3,4-dihydroisoquinoline-2(1H)-carboxylate. Solifenacin possesses asymmetric carbon atoms, and stereoisomers exist based on this atom. Stereoisomers of solifenacin are also preferred as the anticholinergic drug in the present invention.

The preferred solifenacin salt is solifenacin succinate, which is an acid addition salt with succinic acid.

Solifenacin can be prepared by methods known per se, for example, the method described in WO1996/20194. Also commercially available products (Vesicare (registered trademark)) can be used as solifenacin succinate.

Tolterodine is (+)-2-{(1R)-3-[bis(1-methylethyl)amino]-1-phenylpropyl}-4-methylphenol.

Tolterodine possesses an asymmetric carbon atom, and a stereoisomer exists based on this atom. The stereoisomer of tolterodine is also preferred as the anticholinergic drug in the present invention.

The preferred tolterodine salt is tolterodine tartrate, which is an acid addition salt with tartaric acid.

Tolterodine can be prepared by methods known per se, for example, the method described in WO1998/29402. Also commercially available products (Detrusitol (registered trademark)) can be used as tolterodine tartrate.

Fesoterodine is 2-[(1R)-3-(dipropan-2-ylamino)-1-phenylpropyl]-4-(hydroxymethyl)phenyl 2-methylpropanoate.

Fesoterodine is a prodrug of 5-hydroxymethyl derivative (CAS No. 207679-81-0) which is a main active metabolite of tolterodine, and rapidly is metabolized to the 5-hydroxymethyl derivative after oral administration (WO1999/58478). The 5-hydroxymethyl derivative which is a common active metabolite of fesoterodine and tolterodine possesses the anticholinergic activity that is equivalent to tolterodine (Pharmacology and Toxicology Vol. 81, 1997, Page 169-172). According to these facts, fesoterodine can show a pharmacological action which is equivalent to the action based on the anticholinergic activity of tolterodine.

Fesoterodine possesses an asymmetric carbon atom, and a stereoisomer exists based on this atom. The stereoisomer of fesoterodine is also preferred as an anticholinergic drug in the present invention.

The preferred fesoterodine salt is fesoterodine fumarate, which is an acid addition salt combined with fumaric acid.

Fesoterodine can be prepared by methods known per se, for example, the method described in WO1999-58478. Also commercially available products (Toviaz (registered trademark)) can be used as fesoterodine fumarate.

The present invention discloses a method for the prevention and/or treatment of Hand-Foot Syndrome, which comprises administering an effective amount of an anticholinergic drug to a mammal (e.g., human, and non-human (e.g., monkey, sheep, cattle, horse, dog, cat, rabbit, rat, mouse), preferably a human (a patient) (hereafter, sometimes abbreviated to "the method of the present invention"), an agent for the prevention and/or treatment of Hand-Foot Syndrome comprising an anticholinergic drug to be used in such method (hereafter, sometimes abbreviated to "the agent of the present invention"), an anticholinergic drug for use in such prevention and/or treatment, and use of an anticholinergic drug for the manufacture of such agent for the prevention and/or treatment, etc.

Hand-Foot Syndrome subject to the prevention and/or treatment by the present invention is caused by administration of an anti-cancer drug, sickle cell disease, and other factors. Hand-Foot Syndrome caused by administration of an anti-cancer drug is preferred. Hand-Foot Syndrome is also known as; Palmar-plantar erythrodysesthesia syndrome, Acral erythema, Chemotherapy-induced acral erythema, Palmar-plantar erythema, and Hand-foot skin reaction. In the present invention, the term of Hand-Foot Syndrome includes all the other convertible terms mentioned above.

In the present invention, the anti-cancer drug means ones which induce Hand-Foot Syndrome among any drugs used in cancer chemotherapy. Anti-cancer drugs include, for example, an alkylating drug, an antimetabolite, a microtubule inhibitor, an antibiotic anti-cancer drug, a topoisomerase inhibitor, a platinum-containing drug, a biologics, a folic acid antagonist, and a molecularly-targeted drug, etc.

An alkylating drug includes, for example, cyclophosphamide (Endoxan (registered trademark)), ifosfamide (ifomide (registered trademark)), nitrosourea, dacarbazine (dacarbazine (registered trademark)), temozolomide (Temodar (registered trademark)), nimustine (nidran (registered trademark)), busulphan (Busulfex (registered trademark)), melphalan (alkeran (registered trademark)), procarbazine (procarbazine hydrochloride (registered trademark)), ranimustine (cymerin (registered trademark)), thiotepa (tespamin (registered trademark)), etc.

An antimetabolite includes, for example, floxuridine (FUDR (registered trademark)), enocitabine (sunrabin (registered trademark)), carmofur (mifurol (registered trademark)), capecitabine (xeloda (registered trademark)), tegafur (futraful (registered trademark)), tegafur uracil (UFT (registered trademark)), tegafur gimeracil oteracil potassium (TS-1 (registered trademark)), gemcitabine (Gemzar (registered trademark)), cytarabine (Cytosar-U (registered trademark)), cytarabine ocfosfate (Starasid (registered trademark)), nelarabine (Arranon G (registered trademark)), fluorouracil (5-FU), fludarabine (Fludara (registered trademark)), pemetrexed (Alimta (registered trademark)), pentostatin (Coforin (registered trademark)), methotrexate, cladribine (Leustatin (registered trademark)), doxifluridine (Furtulon (registered trademark)), hydroxycarbamide (Hydrea (registered trademark)), mercaptopurine (Leukerin (registered trademark)), etc.

A microtubule inhibitor includes, for example, vinorelbine (Navelbine (registered trademark)), vinblastine (Exal (registered trademark)), vincristine (oncovin (registered trademark)), vindesine (Fildesin (registered trademark)), docetaxel (Taxotere (registered trademark)), paclitaxel (taxol (registered trademark)), etc.

An antibiotic anti-cancer drug includes, for example, mitomycin C (Mitomycin (registered trademark)), doxorubicin (Adriacin (registered trademark)), epirubicin (epirubicin hydrochloride (registered trademark)), daunorubicin (Daunomycin (registered trademark)), bleomycin (Bleo (registered trademark)), actinomycin-D (Cosmegen (registered trademark)), aclarubicin (Aclacinon (registered trademark)), idarubicin (Idamycin (registered trademark)), pirarubicin (Pinorubin (registered trademark)), peplomycin (Pepleo (registered trademark)), mitoxantrone (Novantrone (registered trademark)), amrubicin (Calsed (registered trademark)), zinostatin stimalamer (Smancs (registered trademark)), liposomal doxorubicin (Doxil (registered trademark)), etc.

A topoisomerase inhibitor includes, for example, irinotecan (CAMPTO (registered trademark)), nogitecan (Hycamtin (registered trademark)), etoposide (Vepesid (registered trademark)), sobuzoxane (Perazolin (registered trademark)), etc.

A platinum-containing drug includes, for example, cisplatin (IA-call (registered trademark)), nedaplatin (Aqupla (registered trademark)), oxaliplatin (Elplat (registered trademark)), carboplatin (Carboplatin (registered trademark)), etc.

A biologics includes, for example, interferon $\alpha$, $\beta$, and $\gamma$, interleukin, ubenimex (bestatin (registered trademark)), freeze-dried BCG (Immunobladder (registered trademark)), etc.

A folic acid antagonist includes, for example, folinate, Levofolinate, etc.

A molecularly-targeted drug includes, for example, rituximab (Rituxan (registered trademark)), alemtuzumab, trastuzumab (Herceptin (registered trademark)), cetuximab (Erbitux (registered trademark)), panitumumab (Vectibix (registered trademark)), imatinib (Gleevec (registered trademark)), dasatinib (Sprycel (registered trademark)), nilotinib (Tasigna (registered trademark)), Gefitinib (Iressa (registered trademark)), erlotinib (Tarceva (registered trademark)), everolimus (Afinitor (registered trademark)), temsirolimus (Torisel (registered trademark)), bevacizumab (Avastin (registered trademark)), sunitinib malate (Sutent (registered trademark)), sorafenib tosilate (Nexavar (registered trademark)), bortezomib (Velcade (registered trademark)), gemtuzumab ozogamicin (Mylotarg (registered trademark)), ibritumomab tiuxetan (Zevalin (registered trademark)), tamibarotene (Amnolake (registered trademark)), tretinoin (Vesanoid (registered trademark)), lapatinib tosilate hydrate (Tykerb (registered trademark)), Thalidomide (Thaled (registered trademark)), Lenalidomide (Revlimid (registered trademark)), etc. Other than molecularly-targeted drug specified here, the following molecularly-targeted drugs can also be included: an inhibitor targeting angiogenesis such as human an epithelial growth factor receptor 2 inhibitor, an epithelial growth factor receptor inhibitor, a Bcr-Abl tyrosine kinase inhibitor, an epithelial growth factor receptor tyrosine kinase inhibitor, a mTOR inhibitor, a vascular endothelial growth factor receptor 2 inhibitor (α-VEGFR-2 antibody); various kinase inhibitors such as a MAP kinase inhibitor; an inhibitor targeting cytokine; a proteasome inhibitor; a molecularly-targeted drug such as an antibody-anticancer drug complex, etc. Antibody is contained in these inhibitors.

In addition, the anti-cancer drugs in the present invention do not only includes ones which have been found out so far in the past but also will be discovered from now onward in the future.

It is preferable that the alkylating drug is cyclophosphamide, melphalan.

It is preferable that the antimetabolite is floxuridine, carmofur, capecitabine, tegafur, tegafur uracil, tegafur gimeracil oteracil potassium, cytarabine, fluorouracil, methotrexate, doxifluridine, hydroxycarbamide, and capecitabine is especially preferred.

It is preferable that the microtubule inhibitor is vincristine, docetaxel, paclitaxel.

It is preferable that the antibiotic anti-cancer drug is doxorubicin, daunorubicin, idarubicin, liposomal doxorubicin.

It is preferable that the topoisomerase inhibitor is etoposide.

It is preferable that the platinum-containing drug is cisplatin, oxaliplatin.

It is preferable that the biologics is interleukin-2.

It is preferable that the molecularly-targeted drug is trastuzumab, sunitinib malate, sorafenib tosilate, lapatinib tosilate hydrate, and especially sunitinib malate or sorafenib tosilate.

In the present invention, it is preferable that the anti-cancer drug is an antimetabolite, or a molecularly-targeted drug.

Combination treatment with more than two kinds of anti-cancer drugs can induce Hand-Foot Syndrome. An example of a combination treatment which can induce Hand-Foot Syndrome is the combination treatment which includes more than one kind of anti-cancer drug stated above. Specific examples of the combination are: capecitabine and letrozole (Femara (registered trademark)), capecitabine and lapatinib tosilate hydrate, capecitabine and trastuzumab, capecitabine and oxaliplatin, capecitabine and docetaxel, capecitabine and cyclophosphamide, etc.

When using the anticholinergic drug for the prevention and/or treatment of Hand-Foot Syndrome, its route of administration can be either oral or parenteral. Parenteral administration, for example, can be systemic administration such as intravenous administration, or local administration such as percutaneous administration. Preferably, it is oral administration or percutaneous administration which can be administered locally.

In case the of administering the anticholinergic drug by the above mentioned methods to a mammal (e.g., a human or a non-human, preferably a human (a patient)), a pharmaceutical composition would be used according to the respective administration form.

A pharmaceutical composition for oral administration includes, for example, a solid composition such as a tablet, a pill, a capsule (hard capsule and soft capsule), a dispersible powder and a granule, etc; a liquid composition such as a water agent, a suspension, an emulsion, a syrup, and an elixir, etc. A tablet includes a sublingual tablet, an adhesive oral patch, an orally fast disintegrating tablet, and an orally disintegrating tablet, etc.

In such solid compositions, the anticholinergic drug may be used alone, or admixed with excipients (e.g. lactose, lactose hydrate, mannitol, D-sorbitol, glucose, crystalline cellulose, microcrystalline cellulose, partially pregelatinized starch, corn starch, potato starch, starch, soy lecithin, xylitol, etc.), binders (e.g. hydroxypropylcellulose, hydroxypropylmethylcellulose, ethylcellulose, methylcellulose, gelatin, polyvinyl alcohol, polyvinyl alcohol partially hydrolyzed, polyvinylpyrrolidone, magnesium metasilicate aluminate, polyethylene glycol (macrogol), soy lecithin, etc.), disintegrants (e.g. cellulose calcium glycolate, low substituted hydroxypropylcellulose, croscarmellose sodium, methylcellulose, crospovidone, etc.), surfactants (e.g. oleic acid, sodium lauryl sulfate, polysorbate 80, etc.), lubricants (e.g. magnesium stearate, calcium stearate, talc, hardened oil, glyceryl behenate, etc.), stabilizers (e.g. xylitol, etc.), solubilizers (e.g. glutamic acid, aspartic acid, soy lecithin, etc.) and so on, and formulated according to common methods. In addition, if necessary, it may be coated with coating agents (e.g. white sugar, gelatin, hydroxypropylcellulose, hydroxypropylmethylcellulose, ethylcellulose, methylcellulose, hydroxypropylmethylcellulose phthalate, methacrylic acid copolymer, titanium oxide, yellow ferric oxide, ferric oxide, carnauba wax, sodium lauryl sulfate, blue no. 2, indigo carmine and indigo carmine aluminium lake, etc.), and may be coated with two or more layers. In the case of a capsule, it may be filled within a capsule film composed mainly of protein such as gelatin, collagen; polysaccharide such as starch, amylase, polygalacturonic acid, agar, carrageenan, arabian gum, gellan gum, xanthan gum, pectin, algin acid; biodegradability plastic such as polylactic acid, polyhydroxy butyric acid, polyglutamic acid; hardened fat such as triglyceride and diglyceride which are neutral fat.

In such liquid compositions, the anticholinergic drug may be dissolved, suspended or emulsified into diluent(s) commonly used in the art (such as purified water, ethanol or a mixture thereof). The liquid compositions may further comprise some additives, such as wetting agents, suspending agents, emulsifying agents, sweetening agents, flavoring agents, aroma, preservatives or buffering agents.

Pharmaceutical compositions for intraarterial administration, intravenous administration, or local injection can be solutions, suspensions, emulsions or solid forms which are dissolved or suspended into a solvent for injection immediately before use. In such pharmaceutical compositions, the anticholinergic drug may be dissolved, suspended or emulsified into a solvent. Examples of the solvent include distilled water for injection, physiological saline, vegetable oil, propylene glycol, polyethylene glycol, alcohol such as ethanol, or a mixture thereof. Furthermore, the pharmaceutical compositions can contain some additives described in Japanese Pharmaceutical Excipients Directory 2000 (edited by Japan Pharmaceutical Excipients Council, issued by Yakuji Nippon, Ltd.), such as stabilizing agents, buffering agents, pH adjusting agents, solvents, solubilizers, suspending agents, emulsifying agents, surfactants, antioxidant, antifoaming agent, isotonizing agent, soothing agents, preservatives, etc. Also, in the case of Infusion preparation for instillation, commonly used ingredients for infusion solution, such as electrolytes (e.g. sodium chloride, potassium chloride, calcium chloride, sodium lactate, sodium dihydrogen phosphate, sodium carbonate, magnesium carbonate), sugars (e.g. glucose, fructose, sorbitol, mannitol, dextran), proteins amino acids (e.g. glycine, aspartic acid, lysin), vitamins (e.g. Vitamin $B_1$, Vitamin C) are included in addition to the above mentioned additive agents. They may be produced by sterilizing in a final step, or may be prepared by aseptic manipulation. They may also be manufactured into sterile solid agents, for example, freeze-dried products, which may be dissolved in sterile water or some other sterile diluent(s) for injection immediately before use.

Pharmaceutical compositions for local injection can be microsphere injections. As for the usage and the manufacturing method of the microsphere, it can be referred to "Development and Application of the micro/nano Fabrication System of Capsules and Fine Particles" (edited by Masumi Koishi, CMC Books, 2003) as necessary. Also, as for the controlled release of a common physiological active substance, it can be referred to "Practice of drug delivery system" (Iyaku Journal Co., Ltd. 1986, Kohei Miyao) as necessary. the aforementioned pharmaceutical composition for microsphere injection would make the anticholinergic drug have sustained release in local areas when injected intramuscularly or preferably subcutaneously. Such microsphere injection can be administered intravenously or intra-arterially as desired.

A pharmaceutical composition for percutaneous administration includes, for example, liquid spray, lotion, ointment, cream, gel, sol, aerosol, cataplasm, plaster, tape, etc. In these compositions, the anticholinergic drug and an oil base which is generally used in external preparations [e.g., a plant oil (e.g., cotton seed oil, sesame oil, olive oil or the like), waxes (e.g., carnauba wax, beeswax or the like), higher hydrocarbons (e.g., white petrolatum, liquid paraffin, plastibase or the like), a fatty acid (e.g., stearic acid, palmitic acid or the like) and an ester thereof, higher alcohols (e.g., cetanol or the like), silicons (e.g., silicon fluid, silicon gum or the like) or the like], a water-soluble base [e.g., polyvinyl alcohol, carboxyvinyl polymer, a solution or high molecular hydrogel of cellulose derivative or the like, polyethylene glycol (macrogol), a polyethylene glycol-polypropylene glycol copolymer, propylene glycol, 1,3-butylene glycol, ethanol, glycerol or the like], an adhesive to be used in tapes [e.g., a synthetic rubber adhesive (e.g., a methacrylic acid ester copolymer, a natural rubber adhesive, a synthetic isoprene or the like), a silicon polymer adhesive or the like], a film base [e.g., polyethylene, polypropylene, a polyethylene-vinyl acetate copolymer, PET, an aluminum laminate or the like], a gel base [e.g., dry agar, gelatin, aluminum hydroxide, silicic acid or the like], or an emulsion base in which a surfactant [e.g., an anionic surfactant (e.g., a fatty acid, saponin, fatty acid sarcoside, an alcohol sulfuric acid ester, an alcohol phosphoric acid ester or the like), a cationic surfactant (e.g., a quaternary ammonium salt, a heterocyclic amine or the like), an ampholytic surfactant (e.g., an alkyl betaine, lysolecithin or the like), a nonionic surfactant (e.g., a polyoxyethylene alkyl ether, a polyoxyethylene sorbitan fatty acid ester, a sucrose fatty acid ester or the like), or the like] or the like are added to the oil base and water-soluble base, and the like are used. Also, as occasion demands, generally used additive agents, such as a surfactant [e.g., an anionic surfactant (e.g., a fatty acid, saponin, fatty acid sarcoside, an alcohol sulfuric acid ester, an alcohol phosphoric acid ester or the like), a cationic surfactant (e.g., a quaternary ammonium salt, a heterocyclic amine or the like), an ampholytic surfactant (e.g., an alkyl betaine, lysolecithin or the like), a nonionic surfactant (e.g., a polyoxyethylene alkyl ether, a polyoxyethylene sorbitan fatty acid ester, a sucrose fatty acid ester or the like), or the like], a thickener [e.g., a cellulose derivative (e.g., carboxymethylcellulose or the like), a polycarboxylic acid (e.g., polyacrylic acid, a methoxymethylene maleic anhydride copolymer or the like), a nonionic water-soluble polymer (e.g., polyvinyl pyrrolidone, polyvinyl alcohol or the like), a stabilizing agent [e.g., an antioxidant (e.g., ascorbic acid, sodium pyrosulfite or the like), a chelating agent (e.g., EDTA or the like) or the like], a pH adjusting agent [e.g., a phosphate buffer, sodium hydroxide or the like], a preservative [e.g., parabens, an alkyl quaternary ammonium salt (e.g., benzalkonium chloride, benzethonium chloride or the like) or the like], an absorption acceleration auxiliary [e.g., a fatty acid and its esters (e.g., oleic acid, isopropyl myristate, isopropyl palmitate, butyl myristate or the like), phospholipids (e.g., phosphatidyl choline and the like), terpenes (e.g., limonene or the like), azacycloalkanes (e.g., Azone (trade name, mfd. by Nelson Research) or the like) or the like] and the like can also be added. These percutaneous administration preparations which comprise anticholinergic drug can be produced in the usual way using the aforementioned various bases, adhesives or other additive agents which are added as occasion demands.

The liquid sprays, lotions, sols or aerosols can be produced by dissolving or dispersing the anticholinergic drug in a solvent such as water, propylene glycol, 1,3-butylene glycol, ethanol and glycerol. Additionally, the aforementioned additive agents can also be added as occasion demands.

The ointments or creams can be produced by mixing the anticholinergic drug with the aforementioned water-soluble base, the aforementioned oil base and/or solvent generally used in said technical field such as water or a plant oil, and applying an emulsification treatment by adding a surfactant as occasion demands. Additionally, the aforementioned additive agents can also be added as occasion demands.

The cataplasm, plasters, or tapes can be produced by coating a solution containing the anticholinergic drug and the aforementioned adhesive (which may contain the aforementioned additives as required) on the surface of aforementioned film bases, and by applying a cross-linking treatment or drying operation as required.

The gels can be produced by pouring a solution containing the anticholinergic drug and the aforementioned gel base (which may contain the aforementioned additives as required) into a mold, and by applying a cross-linking treatment or drying operation as required.

The dose of the anticholinergic drug can be any amount as long as it is a dose which shows the efficacy for Hand-Foot Syndrome without significant toxicity of the anticholinergic drug. In general, it is used within the range of from about 0.01 mg to about 200 mg. In this connection, when the administration method is changed as described in the above, the dose necessary for obtaining the desired effect is also changed, so that a suitable dose may be selected according to the administration method, when the anticholinergic drug is administered.

In the case of administering imidafenacin orally, for example, a preferred dose per each administration is from about 0.025 mg to about 0.8 mg, a more preferred dose is from about 0.05 mg to about 0.4 mg, an even more preferred dose is from about 0.1 mg to about 0.2 mg, and the most preferred dose is about 0.1 mg or about 0.2 mg. Also, in the case of percutaneous administration, for example, a preferred dose per each administration is from about 0.05 mg to about 5 mg, a more preferred dose is about 0.1 mg to about 2 mg, and an even more preferred dose is about 0.2 mg to about 1 mg.

In the case of administering solifenacin succinate orally, for example, a preferred dose per each administration is from about 1 mg to about 50 mg, a more preferred dose is from about 2.5 mg to about 20 mg, an even more preferred dose is from about 5 mg to about 10 mg, and the most preferred dose is about 5 mg.

In the case of administering tolterodine tartrate orally, for example, a preferred dose per each administration is from about 0.5 mg to about 20 mg, a more preferred dose is from about 1 mg to about 8 mg, an even more preferred dose is from about 2 mg to about 4 mg, and the most preferred dose is about 4 mg.

In the case of administering fesoterodine fumarate orally, for example, a preferred dose per each administration is from about 1 mg to about 40 mg, a more preferred dose is from about 2 mg to about 16 mg, an even more preferred dose is from about 4 mg to about 8 mg, and the most preferred dose is about 4 mg or about 8 mg.

In the case of using an anticholinergic drug as an agent for the prevention and/or treatment of Hand-Foot Syndrome, the administration period may be any period as long as it is effective. Also, as occasion demands, the anticholinergic drug may be intermittently administered by arranging an appropriate cessation interval.

Examples of the illustrative administration period of the agent of the present invention include from one day to five years, from one day to one year, from one day to six months, and from one day to two months, etc.

Examples of the administration frequency per day during these administration periods include, in the case of the administration forms of oral administration and intravenous administration, from one to 10 times. In the case of the administration forms of oral administration, preferred administration frequency per day is from one to three times, more preferred administration frequency per day is from one to two times, and even more preferred administration frequency per day is one or two times. As for percutaneous administration, administration frequency can be, for example, twice a day, once a day, or once every two to seven days, and the preferred administration frequency is once a day or once every two to four days.

In the present invention, the agent of the present invention can be administered before onset or the recurrence of Hand-Foot Syndrome for the preventive purpose, as well as after the pathogenesis of Hand-Foot Syndrome for the therapeutic purpose.

In the present invention, the administration of the agent of the present invention may be started simultaneously, before or after the administration of anti-cancer drug which induce Hand-Foot Syndrome. For example, a combination of the agent of the present invention and an anti-cancer drug in chemotherapy is possible, and the dose amount of the anti-cancer drug can be the same as the effective dose used for the normal chemotherapy.

In the present invention, the preventive and/or treatment effect of the anticholinergic drug against Hand-Foot Syndrome can be evaluated, for example, by the criteria of Hand-Foot Syndrome in Table 1, Table 2, and Table 3 as shown below. Table 1 is the criteria proposed by Blum, and appeared on page 485-493 in volume 17 of Journal Clinical Oncology published in 1999. Grade 0 is not referred to in this table, but it is understood as grade 0 if no symptom is observed. Table 2 is the National Cancer Institute-Common Toxicity Criteria Version 2.0 (NCI-CTC v2.0), and Table 3 is the National Cancer Institute-Common Terminology Criteria for Adverse Events Version 3.0 (NCI-CTCAE v3.0). Grade 0 is also not referred to in Table 3, but it is understood as grade 0 if no symptom is observed.

TABLE 1

| Grade | Clinical domain | Functional domain |
|---|---|---|
| 1 | Numbness, dysesthesia/paraesthesia, tingling, painless swelling or erythema | Discomfort that does not disrupt normal activities |
| 2 | Painful erythema, with swelling | Discomfort that affects activities of daily living |

TABLE 1-continued

| Grade | Clinical domain | Functional domain |
|---|---|---|
| 3 | Moist desquamation, ulceration, blistering, severe pain | Severe discomfort, unable to work or perform activities of daily living |

If the grade of applicable symptoms in both criteria (clinical area, functional area) does not match, the more applicable grade should be adopted.

TABLE 2

| Grade | Symptoms etc. |
|---|---|
| 0 | None |
| 1 | skin changes or dermatitis without pain |
| 2 | skin changes with pain, not interfering with function |
| 3 | skin changes with pain, interfering with function |

TABLE 3

| Grade | Symptoms etc. |
|---|---|
| 1 | Minimal skin changes or dermatitis without pain |
| 2 | Skin changes or pain not interfering with function |
| 3 | Ulcerative dermatitis or skin changes with pain interfering with function |

In either of these criteria in Table 1, 2, and 3, dose reduction, interruption or discontinuation of the anti-cancer drug might be necessary if a grade of 2 or higher occurs. Therefore, it is necessary to suppress the symptom of Hand-Foot Syndrome to a grade of 1 or lower in order to continue the appropriate cancer treatment as well as to maintain or improve the patient's QOL.

In the present invention, the term "treatment" means to alleviate symptoms of Hand-Foot Syndrome. Specifically, for example, it means to improve subjective symptoms of patients or bring more than one grade down compared to the grade before administering the anticholinergic drug, preferably to Grade 1 or lower.

In the present invention, the term "prevention" means to prevent pathogenesis of Hand-Foot Syndrome, or maintain the mild symptoms, for example, maintain grade 1, when it is occurred. In addition, prevention also means prevention of recurrence of Hand-Foot Syndrome (recurrence prevention).

In the present invention, the anticholinergic drug can be used as a single drug or combined with another drug used for Hand-Foot Syndrome treatment, another coping method of Hand-Foot Syndrome, and/or a drug other than the anti-cancer drug used for the cancer treatment.

When the anticholinergic drug is used in combination with another drug, it may be administered in the form of a combination drug in which both components are formulated in one preparation or may be used in a form in which they are administered as separate preparations. The administration as separate preparations includes simultaneous administration and administration at a different time.

The other drug used for Hand-Foot Syndrome treatment includes, for example, a moisturizing agent, an antibiotic, a topical steroid, a steroid for internal use, a nonsteroidal anti-inflammatory drug, a vitamin $B_6$ preparation, etc.

In the present invention, the moisturizing agent includes, for example, a urea preparation (e.g., urea (Urepearl (registered trademark), Keratinamin (registered trademark), Pastaron (registered trademark)), a heparinoid preparation (e.g., heparinoid (Hirudoid (registered trademark), Hirudoid soft (registered trademark)), a vitamin ointment (e.g., Vitamin A oil (Saline (registered trademark)), a tocopherol vitamin A oil containing vitamin E (Juvela (registered trademark)), a guaiazulene ointment (e.g., Azulene sodium sulfonate hydrate (Azulene)), white Vaseline, etc.

In the present invention, the antibiotic includes, for example, gentamicin sulfate (Gentacin (registered trademark)), fradiomycin sulfate, Sodium Fusidate, etc.

In the present invention, the topical steroid includes, for example, clobetasol propionate (Dermovate (registered trademark)), diflorasone diacetate (Diflal (registered trademark), mometasone furoate (Fulmeta (registered trademark)), betamethasone butyrate propionate (Antebate (registered trademark)), fluocinonide (Topsym (registered trademark)), betamethasone dipropionate (Rinderon DP (registered trademark)), difluprednate (Myser (registered trademark)), amcinonide (Visderm (registered trademark)), diflucortolone valerate (Texmeten (registered trademark)), hydrocortisone butyrate propionate (Pandel (registered trademark)), deprodone propionate (Ecler (registered trademark)), dexamethasone propionate (Methaderm (registered trademark)), dexamethasone valerate (Voalla (registered trademark)), halcinonide (Adcortin (registered trademark)), betamethasone valerate (Betnevate (registered trademark)), betamethasone valerate.gentamicin sulfate (Rinderon VG (registered trademark)), beclomethasone dipropionate (Propaderm (registered trademark)), fluocinolone acetonide (Flucort (registered trademark)), etc.

In the present invention, the steroid for internal use includes, for example, prednisolone, methyl prednisolone, dexamethasone, betamethasone, etc.

In the present invention, the nonsteroidal anti-inflammatory drug includes, for example, acetylsalicylic acid, ibuprofen, loxoprofen sodium, acetaminophen, diclofenac sodium, celecoxib, etc.

In the present invention, the vitamin $B_6$ preparation includes, for example, pyridoxine hydrochloride, pyridoxal phosphate (pyridoxal phosphate hydrate (Pydoxal (registered trademark)), etc.

In the present invention, the other coping method of Hand-Foot Syndrome includes, for example, immersing the hands and feet in cool water; avoiding the hands and feet from being subjected to extremes of temperature, pressure, and friction; cushioning sore skin with soft pads; for treatments of symptoms on nail, washing, protecting with gauze, taping, onychoplasty, artificial nail, cryosurgery, and so on.

The drug other than the anti-cancer drug used for cancer treatment includes, for example, a drug used for cancer pain, a drug for reducing adverse effects of anti-cancer drug, etc.

The drug used for cancer pain includes, for example, a nonsteroidal anti-inflammatory drug, morphine, fentanyl, oxycodone, codeine phosphate, etc.

The drug for reducing adverse effects of anti-cancer drug includes, for example, an antiemetic, an appetite stimulant, a drug effective for treating anemia, a drug effective for treating neutropenia, and a drug effective for peripheral nerve disorder associated with cancer chemotherapy.

The antiemetic includes, for example, a neurokinin1 receptor antagonist (e.g., aprepitant, fosaprepitant dimeglumine), a $5HT_3$ receptor antagonist (e.g., granisetron hydrochloride, ondansetron hydrochloride, azasetron hydrochloride, palonosetron hydrochloride), an antidopaminergic agent (e.g., metoclopramide), a steroid drug (e.g., dexamethasone, methylprednisolone, betamethasone), benzodiazepine, etc.

The appetite stimulant includes, for example, hydrochloric acid lemonade, ghrelin mimetics (anamorelin hydrochloride), etc.

The drug effective for treating anemia includes, for example, erythropoietin preparation (epoetin alfa), etc.

The drug effective for treating neutropenia includes, for example, human granulocyte colony stimulating factor (G-CSF), etc.

The drug effective for peripheral nerve disorder associated with cancer chemotherapy includes for example, $PGE_1$ preparation (limaprost alfadex), etc.

The aforementioned drugs which can be used in combination with the anticholinergic drug are examples and are not limited thereto. The administration method of these drugs is not particularly limited and may be either oral administration, or parenteral administration. In addition, these drugs may be administered in combination with two or more kinds. Based on the above mentioned mechanism, these drugs include the ones already found and the ones will be found in the future.

[Toxicity]

The anticholinergic drug has very low toxicity and is considered to be safe enough for pharmaceutical use.

EXAMPLES

Although the present invention will be described in more detail by the following Examples, it is not limited thereto. In case 1-4, STAYBLA (registered trademark) tablet or URITOS (registered trademark) tablet as imidafenacin was used. In case 5, VESICARE (registered trademark) tablet as solifenacin succinate was used. In case 6, DETRUSITOL (registered trademark) capsule as tolterodine tartrate was used.

Example 1

Effect of Imidafenacin on Hand-Foot Syndrome Caused by Capecitabine Administration <Case 1>

We examined the effect of imidafenacin in a recurrent breast cancer patient (female) with Hand-Foot Syndrome caused by the combination treatment of capecitabine (method B: 2400 mg/day, it is administered orally for 2 consecutive weeks, followed by 1 week rest period; the administration is repeated with this taken as one course) and letrozole 2.5 mg/day.

The degree of Hand-Foot Syndrome was evaluated by the criteria in Table 1 shown above, and the evaluation results were shown in FIG. 1.

Grade 3 hand-foot syndrome appeared in the patient at the end of the third course of capecitabine. At that time, Imidafenacin 0.1 mg was orally administered to the patient twice a day.

As a result, imidafenacin had improved the degree of Hand-Foot Syndrome to grade 1 only 14 days after beginning the treatment. Furthermore, another course of treatment had not caused any aggravation of Hand-Foot Syndrome and grade 1 was maintained, and therefore the anti-cancer treatment could be continued without changing the cancer chemotherapy (i.e., without a dose reduction of the anti-cancer drug or the interruption/discontinuation of the anti-cancer drug was not scheduled).

Thus, it was revealed that imidafenacin is effective for the treatment and prevention of Hand-Foot Syndrome caused by capecitabine, or the combination treatment of capecitabine and letrozole.

Example 2

Effect of Imidafenacin on Hand-Foot Syndrome Caused by Sunitinib Malate Administration <Case 2>

We examined the effect of imidafenacin in a male patient with kidney cancer who developed Hand-Foot Syndrome caused by the administration of sunitinib malate (sunitinib 50 mg/day, it is administered orally for 4 consecutive weeks, followed by a 2 week rest period; the administration is repeated with this taken as one course).

Figure 2:
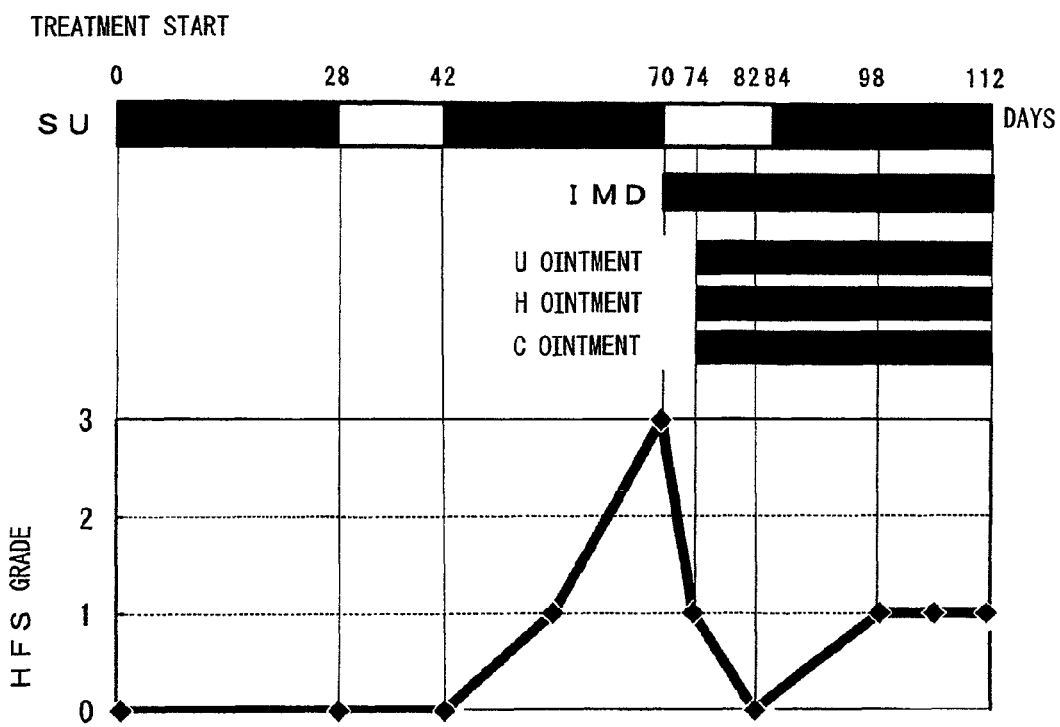
FIG. 2 It shows the effect of imidafenacin on Hand-Foot Syndrome caused by sunitinib malate administration. In the figure, SU, IMD, U ointment, H ointment, C ointment, and HFS represent sunitinib malate, imidafenacin, urea ointment, heparinoid ointment, clobetasol propionate ointment, and Hand-Foot Syndrome, respectively.

The degree of Hand-Foot Syndrome was evaluated by the criteria in Table 1 shown above, and the evaluation results were shown in FIG. 2.

Grade 3 hand-foot syndrome appeared in the patient at the end of the administration of sunitinib in the second course. At that time, Imidafenacin 0.1 mg was orally administered to the patient twice a day.

As a result, imidafenacin had improved the degree of Hand-Foot Syndrome to grade 1 only 4 days after beginning the treatment. Then, a dermatologist prescribed a urea ointment and a heparinoid ointment as a moisturizing agent and a clobetasol propionate ointment, which is a topical steroid with anti-inflammatory activity, and they were used in combination with imidafenacin. After eight days of such treatment, a full recovery from Hand-Foot Syndrome was observed. Furthermore, although the Hand-Foot Syndrome was deteriorated to grade 3 by 4 weeks' sunitinib malate administration in the second course, the patient experienced only grade 1 Hand-Foot Syndrome in the third course as a result of continuing such treatment.

Based on these facts, it was revealed that imidafenacin is effective for the treatment and prevention of Hand-Foot Syndrome caused by sunitinib malate.

Example 3

Effect of Imidafenacin on Hand-Foot Syndrome Caused by Sorafenib Tosilate Administration <Case 3>

We examined the effect of imidafenacin in a male patient with kidney cancer who developed Hand-Foot Syndrome caused by sorafenib tosilate administration (sorafenib 800 mg/day).

Figure 3:
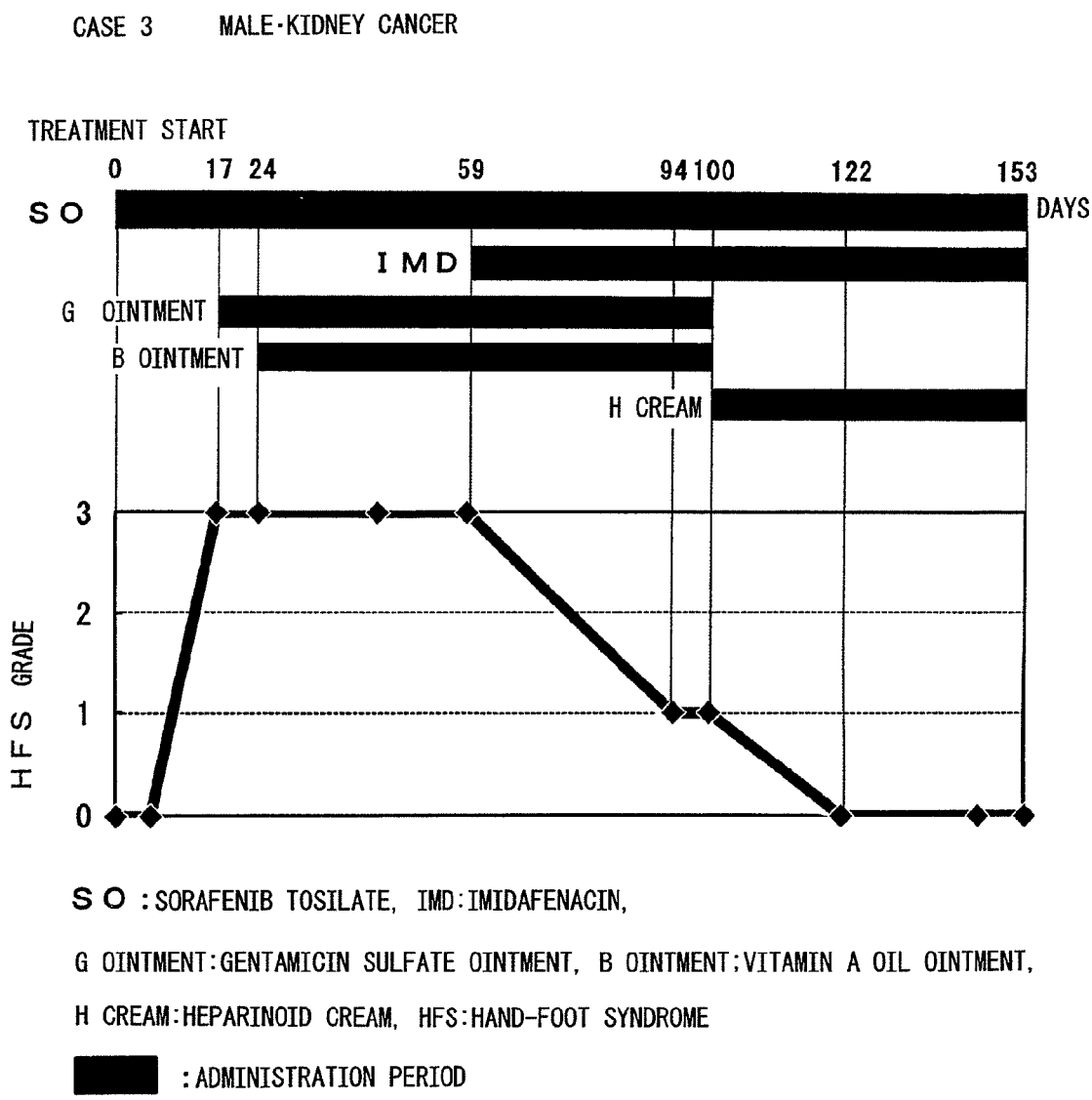
FIG. 3 It shows the effect of imidafenacin on Hand-Foot Syndrome caused by sorafenib tosilate administration. In the figure, SO, IMD, G ointment, B ointment, H cream, and HFS represent sorafenib tosilate, imidafenacin, gentamicin sulfate ointment, vitamin A oil ointment, heparinoid cream, and Hand-Foot Syndrome, respectively.

The degree of Hand-Foot Syndrome was evaluated by the criteria in Table 1 shown above, and evaluation results were shown in FIG. 3.

The patient developed grade 3 Hand-Foot Syndrome immediately after the sorafenib tosilate administration, and he was prescribed gentamicin sulfate ointment as an antibiotic, followed by a vitamin A oil ointment as a moisturizing agent. However, the Hand-Foot Syndrome remained unchanged after 35 days of the additional prescription of the vitamin A oil ointment.

Thus, from this point on, Imidafenacin 0.1 mg was orally administered to the patient twice a day in addition to the gentamicin sulfate ointment and vitamin A oil ointment.

As a result, the symptoms of Hand-Foot Syndrome had been improved to grade 1 at 35 days after beginning the treatment (at the next hospital visit). It is obvious that this effect is due to the imidafenacin because the additional prescription of imidafenacin had showed efficacy against the Hand-Foot Syndrome caused by the sorafenib tosilate, which was not improved by the gentamicin sulfate ointment and vitamin A oil ointment. Furthermore, the combination drug was switched from the gentamicin sulfate ointment and vitamin A oil ointment to the heparinoid cream as the moisturizing agent along with the improvement against the Hand-Foot Syndrome, and oral administration of imidafenacin was continued in combination of the heparinoid cream. After 22 days, he had made a full recovery from the Hand-Foot Syndrome. In addition, after full recovery, recurrence of Hand-Foot Syndrome was prevented by continuous administration of imidafenacin and the moisturizing agent.

Thus, it was revealed that imidafenacin is effective for the treatment and prevention of Hand-Foot Syndrome caused by sorafenib tosilate.

<Case 4>

We examined the effect of imidafenacin in a female patient with kidney cancer who developed Hand-Foot Syndrome caused by sorafenib tosilate administration.

Figure 4:
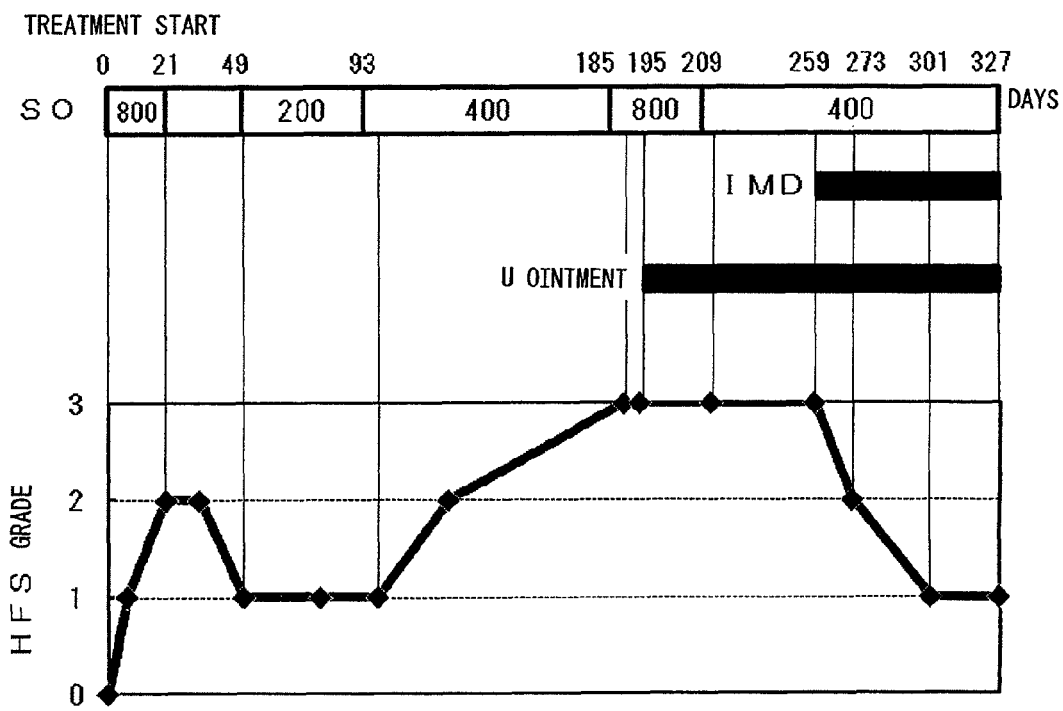
FIG. 4 It shows the effect of imidafenacin on Hand-Foot Syndrome caused by sorafenib tosilate administration. In the figure, SO, IMD, U ointment, and HFS represent sorafenib tosilate, imidafenacin, urea ointment, and Hand-Foot Syndrome, respectively.

The degree of Hand-Foot Syndrome was evaluated by the criteria in Table 1 shown above, and evaluation results were shown in FIG. 4.

The patient developed grade 2 Hand-Foot Syndrome after 21 days from the commencement of the administration of sorafenib tosilate (sorafenib 800 mg/day), so that sorafenib administration was interrupted. The patient recovered to grade 1 on the $28^{th}$ day from the interruption, and then the administration of sorafenib tosilate was restarted at dose ramp-up (starting at 200 mg/day and then gradually increasing the dose). The patient again developed Hand-Foot Syndrome, and it was deteriorated to grade 3 by the dose of sorafenib 800 mg/day. Although a urea ointment as a moisturizing agent was prescribed and the dose of the sorafenib tosilate was reduced (sorafenib 400 mg/day), no improvement was observed even on the $50^{th}$ day after the dose reduction.

From this point, Imidafenacin 0.1 mg was orally administered to the patient twice a day in addition to the urea ointment.

As a result, the Hand-Foot Syndrome had been gradually improved by the administration of the imidafenacin and it's degree was improved to grade 1 at 42 days after the beginning of the imidafenacin treatment. It is obvious that this effect is due to imidafenacin because the additional prescription of imidafenacin had showed efficacy against Hand-Foot Syndrome caused by sorafenib tosilate, which was not improved by the urea ointment and the dose reduction of the sorafenib tosilate. Additionally, the Hand-Foot Syndrome remained as grade 1.

Based on these facts, it was revealed that imidafenacin is effective for the treatment and prevention of Hand-Foot Syndrome caused by sorafenib tosilate.

Also, considering the results of case 1 to 4, it is clear that imidafenacin is effective for Hand-Foot Syndrome regardless of the kind and regimen of the administered anti-cancer drug which is its pathogenesis.

Example 4

Effect of Solifenacin Succinate on Hand-Foot Syndrome Caused by Sorafenib Tosilate Administration <Case 5>

We examined the effect of solifenacin succinate in a male patient with kidney cancer who developed Hand-Foot Syndrome caused by sorafenib tosilate administration (sorafenib 800 mg/day).

Figure 5:
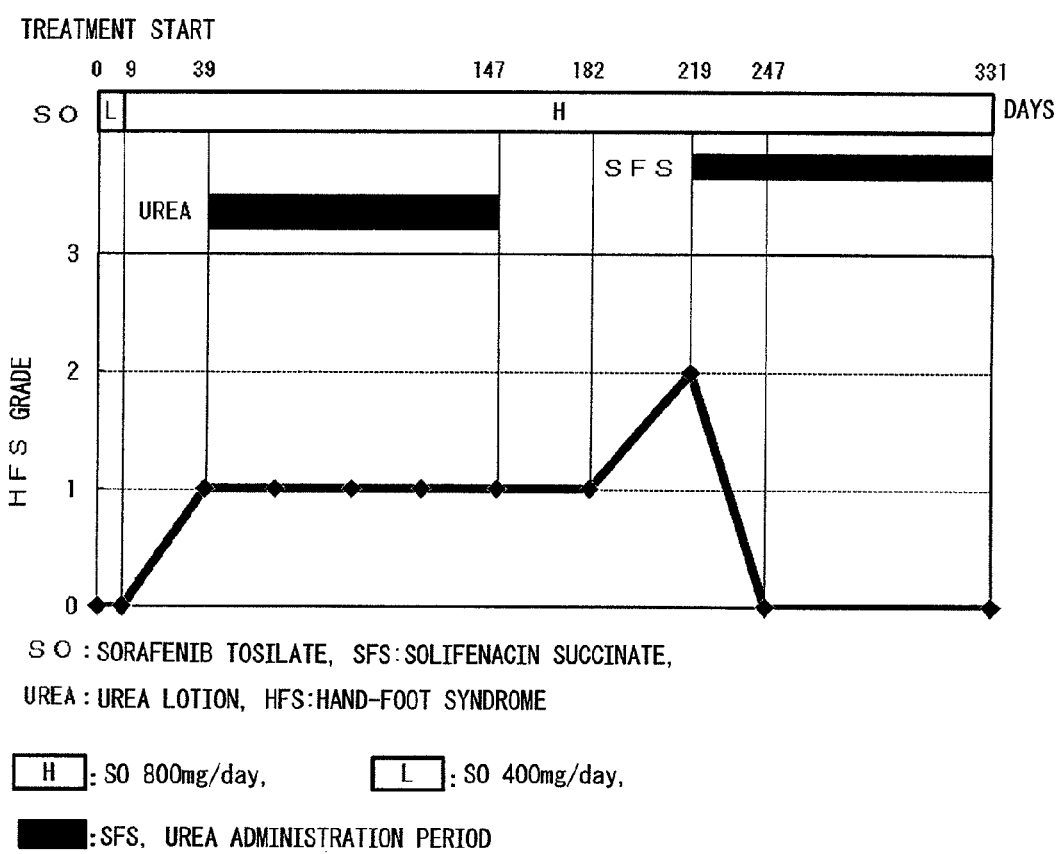
FIG. 5 It shows the effect of solifenacin succinate on Hand-Foot Syndrome caused by sorafenib tosilate administration. In the figure, SO, SFS, UREA and HFS represent sorafenib tosilate, solifenacin succinate, urea lotion, and Hand-Foot Syndrome, respectively.

The degree of Hand-Foot Syndrome was evaluated by the criteria in Table 1 shown above, and evaluation results were shown in FIG. 5.

The patient developed grade 2 Hand-Foot Syndrome accompanied with pain by the administration of sorafenib tosilate (sorafenib 800 mg/day). Therefore, from this point, solifenacin succinate 5 mg was orally administered to the patient once a day, and he had made a full recovery from the Hand-Foot Syndrome at 28 days after the beginning of the solifenacin succinate administration (at the next hospital visit). In addition, the recurrence of the Hand-Foot Syndrome was prevented by the continuous administration of solifenacin succinate after his full recovery.

It was revealed that solifenacin succinate is effective for the treatment and prevention of Hand-Foot Syndrome caused by sorafenib tosilate.

Example 5

Effect of Tolterodine Tartrate on Hand-Foot Syndrome Caused by Sorafenib Tosilate Administration <Case 6>

We examined the effect of tolterodine tartrate in a male patient with kidney cancer who developed Hand-Foot Syndrome caused by sorafenib tosilate administration.

Figure 6:
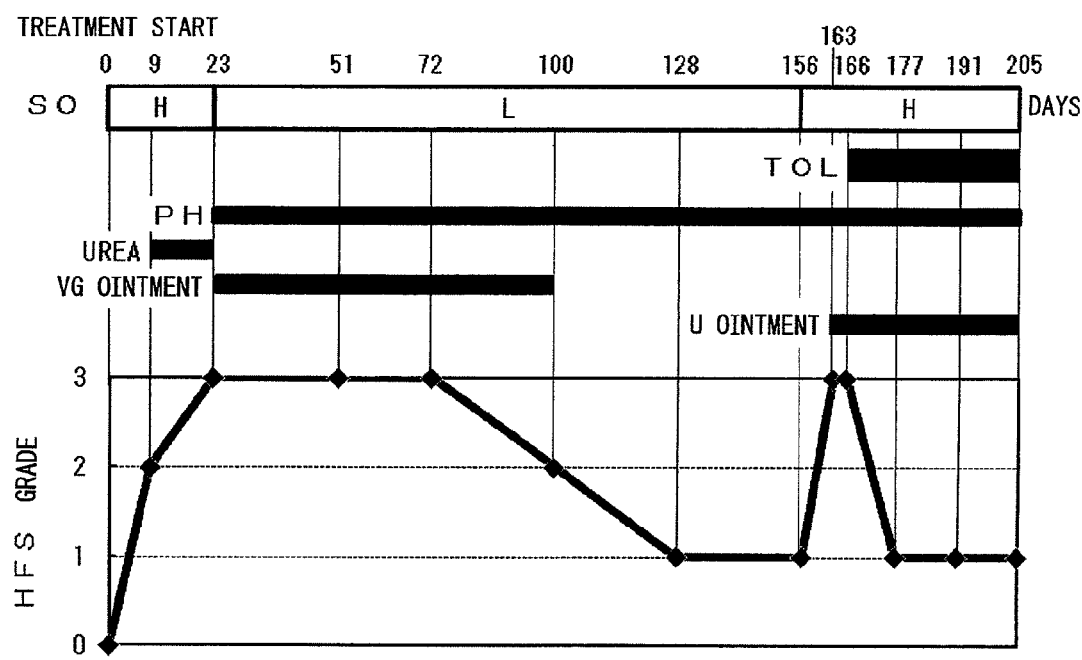
FIG. 6 It shows the effect of tolterodine tartrate on Hand-Foot Syndrome caused by sorafenib tosilate administration. In the figure, SO, TOL, PH, U ointment, UREA, VG ointment and HFS represent sorafenib tosilate, tolterodine tartrate, pyridoxine hydrochloride, urea ointment, UREA lotion, betamethasone valerate and gentamicin sulfate ointment, and Hand-Foot Syndrome, respectively.

The degree of Hand-Foot Syndrome was evaluated by the criteria in Table 1 shown above, and evaluation results were shown in FIG. 6.

The patient developed grade 2 Hand-Foot Syndrome by sorafenib tosilate administration (sorafenib 800 mg/day). Urea lotion was prescribed, but the symptoms had not been improved and then the degree of Hand-Foot Syndrome was deteriorated to grade 3.

Thus, the dose of sorafenib tosilate was reduced (sorafenib 400 mg/day), and pyridoxine hydrochloride, betamethasone valerate and gentamicin sulfate ointment were prescribed. Then the patient had recovered to grade 1 after 105 days from the commencement of the dose reduction of sorafenib tosilate. (Administration of betamethasone valerate and gentamicin sulfate ointment was discontinued when the degree of Hand-Foot Syndrome had been improved to grade 2.)

Then the dose of sorafenib tosilate was increased (sorafenib 800 mg/day) in response to the improvement of Hand-Foot Syndrome to grade 1. However, the symptoms of Hand-Foot Syndrome had been again deteriorated to grade 3, and even with the prescription of urea ointment in addition to pyridoxine hydrochloride, the Hand-Foot Syndrome showed no improvements.

Therefore, from this point, tolterodine tartrate 4 mg was orally administered to the patient once a day in addition to the pyridoxine hydrochloride and urea ointment.

As a result, only 11 days from the commencement of the tolterodine tartrate administration, the degree of Hand-Foot Syndrome had been improved to grade 1. It is obvious that this effect is due to the tolterodine tartrate because the additional prescription of tolterodine tartrate had showed pronounced efficacy in a short term against the Hand-Foot Syndrome caused by the sorafenib tosilate (sorafenib 800 mg/day), which was not improved by pyridoxine hydrochloride and urea. In addition, as a result of continuing such treatment, the Hand-Foot Syndrome was not again deteriorated and remained as grade 1 even by continuation of administration of sorafenib tosilate as sorafenib 800 mg/day. Therefore, the anti-cancer treatment could be continued without changing the cancer chemotherapy (dose reduction of the anti-cancer drug or interruption/discontinuation of the anti-cancer drug was not scheduled).

Based on these facts, it was revealed that tolterodine tartrate is effective for the treatment and prevention of Hand-Foot Syndrome caused by sorafenib tosilate.

Hand-Foot Syndrome is an intractable condition in which a patient does not recover easily even if the anti-cancer drug which caused Hand-Foot Syndrome was interrupted, or a moisturizing agent or the like was prescribed. Nevertheless, as the aforementioned examples proved, patients can surprisingly recover completely or almost completely from the Hand-Foot Syndrome by administration of an anticholinergic drug in accordance with the present invention, even without dose reduction, interruption or discontinuation of the drug that caused the Hand-Foot Syndrome. Imidafenacin, solifenacin, and tolterodine, the drugs used in aforementioned examples, are classified according to their antagonism into antagonist selective for M1 and M3 muscarinic receptor, M3 selective muscarinic receptor antagonist, and subtype nonselective muscarinic receptor antagonist respectively, and although they have anticholinergic activity in common, they do not necessarily show the same antagonism. In addition, imidafenacin (the basic skeleton of which is an imidazole ring), solifenacin (the basic skeleton of which is a quinuclidine ring) and tolterodine (which is a phenol derivative) do not possess a common structural character, and their commonality is only that of anticholinergic activity. Nevertheless, these three example drugs are all proven to be effective to Hand-Foot Syndrome, and therefore it is obvious that any drug with anticholinergic activity would be effective for treatment and prevention of Hand-Foot Syndrome as well as these example drugs regardless of its structure or its antagonism. As there may be differences in the effectiveness of individual anticholinergic drugs, the fact that the anticholinergic drug is effective for the prevention and treatment of Hand-Foot Syndrome regardless of its kind makes it possible to choose the most effective anticholinergic drug for each patient, providing for a wide selection of prescription drugs, and therefore it is very beneficial.

INDUSTRIAL APPLICABILITY

The agent for the prevention and/or treatment of Hand-Foot Syndrome comprising a compound with anticholinergic activity disclosed herein is indeed useful as a medicine, as it can be safely administered to patients with Hand-Foot Syndrome, and it has shown a superior preventive and/or treatment effect against Hand-Foot Syndrome. Until now, dose reduction, interruption or discontinuation of the anti-cancer drug was required to manage hand-foot syndrome. However, the use of the agent of the present invention enables patients to continue the appropriate cancer treatment and also improves the QOL of the patients by treating and preventing Hand-Foot Syndrome.

The invention claimed is:

1. A method for the recurrence prevention and/or treatment of Hand-Foot Syndrome, which comprises administering an effective amount of an M3 muscarinic receptor antagonist to a mammal in need thereof, in an amount effective for the recurrence prevention and/or treatment of Hand-Foot Syndrome, wherein the Hand-Foot Syndrome is caused by administration of an anti-cancer drug.

2. The method according to claim 1, wherein the M3 muscarinic receptor antagonist is one or more compounds selected from the group consisting of a M3 selective muscarinic receptor antagonist, an antagonist selective for a M1 and a M3 muscarinic receptor and a subtype nonselective muscarinic receptor antagonist.

3. The method according to claim 2, wherein the M3 muscarinic receptor antagonist is a compound selected from the group consisting of imidafenacin, solifenacin, tolterodine and fesoterodine, or a pharmaceutically acceptable salt or solvate thereof.

4. The method according to claim 3, wherein the compound is a compound selected from the group consisting of imidafenacin, solifenacin succinate, tolterodine tartrate and fesoterodine fumarate.

5. The method according to claim 1, wherein the M3 muscarinic receptor antagonist is imidafenacin, or a pharmaceutically acceptable salt or solvate thereof.

6. The method according to claim 1, wherein the anti-cancer drug is an antimetabolite or a molecularly-targeted drug.

7. The method according to claim 6, wherein the antimetabolite is capecitabine and the molecularly-targeted drug is sunitinib malate or sorafenib tosilate.

8. A method for the recurrence prevention and/or treatment of Hand-Foot Syndrome, which comprises administering an effective amount of imidafenacin, or a pharmaceutically acceptable salt or solvate thereof, to a mammal in need thereof, in an amount effective for the recurrence prevention and/or treatment of Hand-Foot Syndrome, wherein the Hand-Foot Syndrome is caused by administration of an anti-cancer drug.

9. A method for the recurrence prevention and/or treatment of Hand-Foot Syndrome, which comprises administering an effective amount of solifenacin, or a pharmaceutically acceptable salt or solvate thereof, to a mammal in need thereof, in an amount effective for the recurrence prevention and/or treatment of Hand-Foot Syndrome, wherein the Hand-Foot Syndrome is caused by administration of an anti-cancer drug.

10. A method for the recurrence prevention and/or treatment of Hand-Foot Syndrome, which comprises administering an effective amount of tolterodine or fesoterodine, or a pharmaceutically acceptable salt or solvate thereof, to a mammal in need thereof, in an amount effective for the recurrence prevention and/or treatment of Hand-Foot Syndrome, wherein the Hand-Foot Syndrome is caused by administration of an anti-cancer drug.

* * * * *